United States Patent [19]

Saito et al.

[11] 4,298,545

[45] Nov. 3, 1981

[54] PROCESS FOR PRODUCING PHTHALONITRILE

[75] Inventors: Masao Saito; Motoyuki Hosokawa; Takamasa Kawakami; Yuko Murayama, all of Niigata, Japan

[73] Assignee: Mitsubishi Gas Chemical Company, Inc., Tokyo, Japan

[21] Appl. No.: 136,989

[22] Filed: Apr. 3, 1980

[30] Foreign Application Priority Data

Apr. 3, 1979 [JP] Japan ................................. 54-39919

[51] Int. Cl.$^3$ ........................................... C07C 121/56
[52] U.S. Cl. ................................ 260/465 H; 564/385
[58] Field of Search ....................... 260/465 C, 465 H

[56] References Cited

U.S. PATENT DOCUMENTS 2,833,807  5/1958  Farkas et al. ................... 260/465 C Primary Examiner—Dolph H. Torrence
Attorney, Agent, or Firm—Armstrong, Nikaido, Marmelstein & Kubovcik

[57] ABSTRACT

Phthalonitrile is produced in a good yield by contacting a xylylenediamine condensate with an oxide catalyst of silica or alumina system in the presence of a molecular oxygen-containing gas or a mixture of a molecular oxygen-containing gas and ammonia.

12 Claims, No Drawings

PROCESS FOR PRODUCING PHTHALONITRILE

This invention relates to a process for producing phthalonitrile from a xylylenediamine condensate as a starting material, and more particularly to a process for producing isophthalonitrile, or terephthalonitrile or a mixture thereof by catalytic oxidation of metaxylylenediamine condensate, or paraxylylenediamine condensate, or a mixture thereof.

In the production of xylylenediamine by catalytic hydrogenation of phthalonitrile, it is known that xylylenediamine condensates having a secondary amino bond (—NH—) in such a condensed form that one ammonia molecule is released from two aminomethyl groups (—CH$_2$NH$_2$) and a Schiff's bond (—CH=N—) in such a condensed form that one ammonia molecule and one hydrogen molecule are released from the two aminomethyl groups are produced as a by-product (Japanese Patent Publication No. 8414/70).

To suppress the formation of such xylylenediamine condensate, addition of ammonia at the catalytic hydrogenation of phthalonitrile, improvement of the catalyst, etc. have been proposed (Japanese Patent Publications Nos. 20969/78 and 22593/73), but the production of xylylenediamine condensate is inevitable in any of these arts.

Xylylenediamine condensate has an expected application as a curing agent for epoxy resin, etc., but have not been fully utilized. It is disclosed in Kogyo Kagaku Zashi, 74 No. 6, 1273-1275 (1971) that hydrolysis of xylylenediamine condensate produces phthalaldehyde and xylylenediamine, but it has not been reported that the hydrolysis is commercially practical.

As a result of extensive study on an effective process for utilizing the xylylenediamine condensate, the present inventors have unexpectedly found that phthalonitrile can be produced in a good yield by contacting xylylenediamine condensate with an oxide catalyst in the presence of a molecular oxygen-containing gas or a mixture of molecular oxygen-containing gas and ammonia, and have established the present invention. A process for producing phthalonitrile from xylylenediamine condensate has not been known so far, and is quite novel.

According to the present invention, carbon monoxide, carbon dioxide and water are produced in addition to phthalonitrile, and other by-products are much less produced. That is, recovery and purification of phthalonitrile can be carried out without difficulty, and the pathalonitrile produced according to the present invention can be reused as such as a starting material for producing xylylenediamine. Accordingly, the present invention has a very great commercial significance in the xylenediamine industry.

The xylylenediamine condensate to be used as a starting material in the present invention is a meta or para-condensate corresponding to meta or para-xylylenediamine, represented by the following general formula:

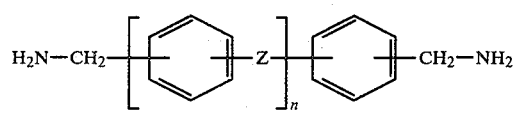

[wherein Z represents —CH=N—CH$_2$— (Schiff's base type bond), or —CH$_2$—NH—CH$_2$— (secondary amino type bond), or a mixture thereof, n is an integer of 1 or more] and also includes a mixture of meta and para-condensates, that is, co-condensate.

In addition to the single condensates and the mixture thereof, the condensates further containing metaxylylenediamine, paraxylylenediamine, or a mixture thereof can be used as the starting material.

The oxide catalyst to be used in the present invention is the ordinary catalyst known as a gas phase oxidation catalyst of:
(1) silica or alumina, or
(2) silica or alumina containing
  (a) vanadium oxide, and
  (b) at least one metal oxide selected from the group consisting of oxides of chromium, molybdenum, tungsten, bismuth, manganese, antimony, iron, boron, phosphorus, tellurium and titanium.

The present catalyst can be prepared according to the well known procedure.

An alumina system oxide catalyst is prepared by adding granular alumina to an aqueous solution of compounds of other catalyst component, evaporating to dryness, drying and calcining in a stream of air.

A silica system oxide catalyst is prepared by adding silica sol to an aqueous solution of compounds of other catalyst component, and, in the case of a fluidized bed catalyst, by spray drying the resulting mixture and calcining in a stream of air, and, in the case of a fixed bed catalyst, by evaporating to dryness, drying and calcining in a stream of air.

The percent by weight of total weight of other oxide than silica or alumina can be varied within the wide range, but the range of 5 to 80 percent by weight is suitable.

The molecular oxygen-containing gas to be used in the present invention is substantially pure oxygen, or a gas mixture containing a portion of inert gas, and it is cheapest and practical to use air.

Phthalonitrile can be obtained through reaction in the presence of only such molecular oxygen-containing gas, and thus the simultaneous presence of ammonia is not essential for the present invention.

However, in conversion of xylylenediamine into phthalonitrile ideally without any loss, the number of nitrogen atom is short for the number of benzene ring in the molecule of xylylenediamine condensate, and therefore the simultaneous presence of ammonia is effective for increasing a phthalonitrile yield, and thus preferable.

The simultaneous presence of ammonia in an amount of 0.1–0.3 times the volume of the oxygen-containing gas is suitable.

The xylylenediamine will have different physical properties, depending upon the degree of condensation, and usually is a solid or a viscous liquid at room temperature. The xylylenediamine condensate has a low vapor pressure, and undergoes considerable thermal decomposition with increasing temperature. Thus, it is difficult to supply it in a gaseous state. In the present invention, xylylenediamine condensate can be supplied to the reaction system in either a liquid state or a solid state, depending upon the mode of reaction. It is particularly advantageous to supply it by spraying, because of good contact with the catalyst.

Rate of supplying the xylylenediamine condensate can be changed in a considerably wide range by properly selecting the reaction conditions, but is preferably in a range of 0.01–0.3 g/hr/ml of catalyst.

Space velocity of molecular oxygen-containing gas can be changed in a considerably wide range by properly selecting the reaction conditions or depending upon the gas composition, and a preferable range of space velocity using air as the oxygen source is 200–4,000 hr$^{-1}$.

Reaction temperature is in a range of 250°–600° C., preferably 300°–500° C. Below the lower limit of the reaction temperature, no satisfactory conversion is obtained, whereas above the upper limit of the reaction temperature, decomposition reaction is increased, and no satisfactory yield is obtained.

Reaction is usually carried out under the atmospheric pressure, but can be carried out under a superatmospheric pressure.

Reaction can be carried out by any of fixed bed type, fluidized bed type, batch type, pass-through type, etc., but in view of the contact of xylylenediamine condensate with the catalyst, controllability of reaction temperature and operability, a fluidized bed type is preferable.

The present invention will be described in detail, referring to Examples, where yield (% by weight) is a percentage of weight of product to weight of starting material xylylenediamine condensate.

EXAMPLE 1

40 ml of catalyst of silica on which oxides of vanadium, a chromium and boron were supported (V:CR:B in atomic ratio = 1:1:0.5; ratio of silica to other oxides by weight32 1:1; average particle size: 60μ; apparent bulk density: 1.0 g/ml), prepared by spray-drying a silica sol slurry containing a vanadium compound, a chromium compound and a boron compound, followed by calcination was filled in a fluidized bed type reactor, 23 mm in inner diameter, heated by molten salt. 1 g/hr of metaxylylenediamine condensate having an average degree of condensation of 4.5 (corresponding to n=3.5 in said general formula) and 25 l/hr of air were supplied to the reactor, and subjected to reaction at 350° C. The metaxylylenediamine condensate was sprayed into the reactor from a nozzle by means of a high pressure microfeeder.

Isophthalonitrile yield was 23% by weight, and only a trace amount of benzonitrile and metatolunitrile, which were presumed to be thermal decomposition products of metaxylylenediamine condensate, was formed.

EXAMPLE 2

Reaction was carried out under the same conditions and in the same manner as in Example 1, except that 5 l/hr of ammonia gas was further supplied to the reaction in addition to the metaxylylenediamine condensate and air.

Isophthalonitrile yield was 51% by weight, and only a trace amount of benzonitrile and metatolunitrile was formed.

EXAMPLE 3

Reaction was carried out under the same conditions in the same manner as in Example 2, except that reaction temperature of 450° C. was used.

Isophthalonitrile yield was 42% by weight, and benzonitrile yield and metatolunitrile yield were 0.8% by weight and 2.1% by weight, respectively.

EXAMPLE 4

Reaction was carried out under the same conditions in the same manner as in Example 1 except that 6 g/hr of metaxylylenediamine, 58 l/hr of air and 13 l/hr of ammonia gas were supplied to the reactor, and reaction temperature of 370° C. was used.

Isophthalonitrile yield was 44% by weight, and only a trace amount of benzonitrile and metatolunitrile was formed.

EXAMPLE 5

Reaction was carried out under the same conditions in the same manner as in Example 2, except that paraxylylenediamine condensate having an average degree of condensation of 4.5 was used in place of the metaxylylenediamine condensate.

Terephthalonitrile yield was 54% by weight, and only a trace amount of benzonitrile and paratolunitrile was formed.

EXAMPLE 6

40 ml of the same catalyst as used in Example 1 and 1 g of powder of the same metaxylylenediamine condensate as used in Example 1 were filled in a fluidized bed type reactor, 23 mm in inner diameter, and fluidized by supplying 25 l/hr of air and 5 l/hr of ammonia gas to the reactor. The reactor was dipped in a molten salt bath heated at 380° C., and the reaction was carried out for one hour.

Isophthalonitrile yield was 46% by weight, and only a trace amount of benzonitrile and metanitrile was formed.

EXAMPLES 7–14

Reaction was carried out under the same conditions in the same manner as in Example 2, except that the kind of catalyst was changed. The result is shown in the following Table, where in the case of catalysts of silica or alumina and other oxides, silica or alumina is designated as carrier for the sake of convenience, and percent by weight of total weight of other oxides than silica or alumina to total weight of catalyst is shown as "supported other oxides". Catalysts of silica as carrier were prepared in the same manner as in Example 1, and catalysts of alumina as carrier were prepared by impregnation method. Single silica catalyst and catalysts of silica as carrier had the particle size of 70μ and the apparent bulk density of 1.0 g/ml, and single alumina catalyst and catalysts of alumina as carrier had the particle size of 60μ and the apparent bulk density of 1.1 g/ml.

TABLE

| Ex. No. | | 7 | 8 | 9 | 10 | 11 | 12 | 13 | 14 |
|---|---|---|---|---|---|---|---|---|---|
| | Catalyst component | $V_2O_5$ $MoO_3$ | $TiO_2$ $V_2O_5$ | Alumina | Silica | $V_2O_5$ $WO_3$ $Sb_2O_3$ | $V_2O_5$ $Fe_2O_3$ $Sb_2O_3$ | $V_2O_5$ $Cr_2O_3$ $TeO_2$ | $V_2O_5$ $MnO$ $Fe_2O_3$ $P_2O_5$ |
| Cata- | Atmic ratio of | V 1 | Ti 1 | | | V 5 | V 5 | V 1 | V 4 |

| lyst | catalyst compo- nent | Mo 0.3 | V 0.06 | | W 3 Sb 3 | Fe 1 Sb 3 | Cr 1 Te 0.1 | Mn 1 Fe 1 P 0.1 |
|---|---|---|---|---|---|---|---|---|
| | Carrier Supported other oxides wt % | Alumina 10 | Silica 30 | | Alumina 10 | Alumina 10 | Silica 30 | Alumina 15 |
| Isophthalo- nitrile yield wt % | | 49 | 33 | 25 20 | 43 | 39 | 47 | 35 |

What is claimed is:

1. A process for producing phthalonitrile, which comprises contacting a xylylenediamine condensate with an oxide catalyst in the presence of a molecular oxygen-containing gas at a reaction temperature of 250°–600° C., said oxide catalyst being a catalyst of (1) silica or alumina, or (2) silica or alumina containing (a) vanadium oxide and at least one metal oxide selected from the group consisting of oxides of chromium, molybdenum, tungsten, bismuth, manganese, antimony, iron, boron, phosphorus, tellurium, and titanium, and said xylylenediamine condensate being a meta or paraxylylene diamine condensate represented by the formula:

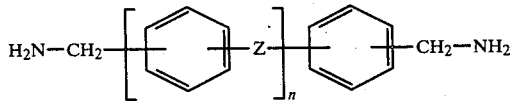

wherein Z is —CH=N—CH$_2$— or —CH$_2$—N-H—CH$_2$— and n is an integer of 1 or more, or a mixture of the meta and paraxylylenediamine condensates.

2. A process according to claim 1, wherein ammonia is present simultaneously.

3. A process according to claim 2, wherein the ammonia in an amount of 0.1–0.3 times the volume of the molecular oxygen-containing gas is present simultaneously.

4. A process according to claim 1, wherein the xylylenediamine condensate further contains metaxylylenediamine, or paraxylylenediamine, or a mixture thereof.

5. A process according to claim 1, wherein the xylylenediamine condensate is supplied to reaction system by spraying.

6. A process according to claim 1, wherein the xylylenediamine condensate is supplied to reaction system at a rate of 0.01–0.3 g/hr/ml of catalyst.

7. A process according to claim 1, where the molecular oxygen-containing gas is air.

8. A process according to claim 7, wherein the air is supplied to reaction system at a space velocity of 200–4,000 hr$^{-1}$.

9. A process according to claim 1, wherein the reaction is carried out at 300°–500° C.

10. A process according to claim 1, wherein the reaction is carried out under the atmospheric pressure or a superatmospheric pressure.

11. A process according to claim 1, wherein the reaction is carried out by fixed bed type or fluidized bed type, or batchwise or pass-throughwise.

12. A process according to claim 11, wherein the reaction is carried out by fluidized bed type.

* * * * *